US011981753B2

(12) United States Patent
Angell et al.

(10) Patent No.: US 11,981,753 B2
(45) Date of Patent: May 14, 2024

(54) PEPTIDE COMPOUND AND APPLICATION THEREOF, AND COMPOSITION CONTAINING PEPTIDE COMPOUND

(71) Applicant: ShangPharma Innovation Inc., Wilmington, DE (US)

(72) Inventors: Yvonne Angell, Shanghai (CN); Yu Wu, Shanghai (CN); Yan Wang, Shanghai (CN); Weimin Liu, Shanghai (CN); Kin Chiu Fong, Shanghai (CN); Jie Wen, Shanghai (CN); Yonghan Hu, Shanghai (CN)

(73) Assignee: ShangPharma Innovation Inc., Wilmington, DE (US)

( * ) Notice: Subject to any disclaimer, the term of this patent is extended or adjusted under 35 U.S.C. 154(b) by 0 days.

(21) Appl. No.: 17/726,604

(22) Filed: Apr. 22, 2022

(65) Prior Publication Data
US 2022/0242908 A1 Aug. 4, 2022

Related U.S. Application Data

(62) Division of application No. 16/628,586, filed as application No. PCT/CN2018/094618 on Jul. 5, 2018, now Pat. No. 11,427,615.

(30) Foreign Application Priority Data

Jul. 5, 2017 (CN) .......................... 201710543383.0
Jul. 4, 2018 (CN) .......................... 201810725881.1

(51) Int. Cl.
*A61K 47/60* (2017.01)
*A61P 35/04* (2006.01)
*C07K 7/06* (2006.01)
*A61K 38/00* (2006.01)

(52) U.S. Cl.
CPC ............... *C07K 7/06* (2013.01); *A61K 47/60* (2017.08); *A61P 35/04* (2018.01); *A61K 38/00* (2013.01)

(58) Field of Classification Search
CPC . C07K 7/06; C07K 7/08; C07K 14/47; A61K 47/60; A61K 38/00; A61K 38/08; A61K 38/10; A61K 38/16; A61P 35/04; A61P 5/00; A61P 15/00; A61P 15/08; A61P 25/24; A61P 35/00
See application file for complete search history.

(56) References Cited

U.S. PATENT DOCUMENTS

| | | | |
|---|---|---|---|
| 6,800,611 B2 | 10/2004 | Fujii et al. | |
| 7,625,869 B2 | 12/2009 | Kitada et al. | |
| 7,754,220 B2 | 7/2010 | Ohtaki et al. | |
| 7,960,348 B2 | 6/2011 | Asami | A61P 15/08 |
| | | | 514/19.8 |
| 8,361,986 B2 | 1/2013 | Kandimalla et al. | |
| 8,592,379 B2 | 11/2013 | Fujii et al. | |
| 8,765,909 B2 | 7/2014 | Asami et al. | |
| 8,878,871 B2 | 11/2014 | Clark et al. | |
| 2004/0180407 A1 | 9/2004 | Watanabe et al. | |
| 2005/0240008 A1 | 10/2005 | Ohtaki et al. | |
| 2009/0093615 A1 | 4/2009 | Asami et al. | |
| 2011/0171160 A1 | 7/2011 | Minamitani | A61K 47/60 |
| | | | 424/78.17 |
| 2015/0361138 A1 | 12/2015 | Beltramo | C07K 7/00 |
| | | | 514/19.3 |

FOREIGN PATENT DOCUMENTS

| | | | | |
|---|---|---|---|---|
| CN | 101341168 A | 1/2009 | | |
| CN | 101341168 B | 1/2013 | | |
| CN | 106544322 A | 3/2017 | | |
| JP | 2003002841 A | 1/2003 | | |
| TW | 201906856 A | 12/2019 | | |
| WO | 0024890 A1 | 5/2000 | | |
| WO | 0175104 A1 | 10/2001 | | |
| WO | 02085399 A1 | 10/2002 | | |
| WO | 2007072997 A1 | 6/2007 | | |
| WO | WO-2009131191 A1 | 10/2009 | ............. | A61P 15/00 |
| WO | 2010033224 A1 | 3/2010 | | |
| WO | WO-2014118318 A1 | 8/2014 | ............. | C07K 7/00 |

OTHER PUBLICATIONS

Quaas et al [Fertility and Sterility, vol. 103, No. 3, Mar. 2015 (Year: 2015).*
Notice of Rejection dated Nov. 29, 2021 issued in corresponding Taiwan Application No. 107123335, with English translation, 14 pages.
First Office Action dated Jun. 15, 2021 issued in Taiwan Application No. 107123335, with English translation, 9 pages.
International Search Report dated Sep. 27, 2018 issued in International Patent Application No. PCT/CN2018/094618 with English translation, 9 pages.
Written Opinion of the International Searching Authority dated Sep. 27, 2018 issued in International Patent Application No. PCT/CN2018/094618 with English translation, 10 pages.
Partial Supplementary European Search Report dated Jul. 17, 2020 issued in corresponding EP Application No. 18828694.2, 13 pages.
Jiang, Fusheng, et al., "Research progress of polyethylene glycol prodrugs," Chin Pharm J, vol. 42, Issue 12, 2007, 13 pages.
Lee, Jeong-Hyung, et al., "KiSS-1, a novel human malignant melanoma metastasis-suppressor gene," Journal of the National Cancer Institute, vol. 88, No. 23, 1996, pp. 1731-1737.
Ohtaki, T., et al., "Metastasis suppressor gene KiSS-1 encodes peptide ligand of a G-protein-coupled receptor," Letters to Nature, vol. 411, Issue 6837, 2001, pp. 613-617.

(Continued)

*Primary Examiner* — Sudhakar Katakam
(74) *Attorney, Agent, or Firm* — SZDC Law PC

(57) ABSTRACT

Disclosed are a peptide compound and an application thereof, and a composition containing the peptide compound. The present invention provides a peptide compound YA-156, and a pharmaceutically acceptable salt, a tautomer, a solvate, a crystal form or a prodrug thereof. The compound has good stability and good activity for Kiss1R.
Palm-PEG8-Gly-Gly-(D-Tyr)-Hyp-Asn-Thr-Phe-azaGly-Leu-Arg (Me)-Trp-NH$_2$ 1 Claim, No Drawings

(56) References Cited

OTHER PUBLICATIONS

Kotani, Masato, et al., "The Metastasis Suppressor Gene KiSS-1 Encodes Kisspeptins, the Natural Ligands of the Orphan G Protein-coupled Receptor GPR54," J. Biol. Chem., vol. 276, 2001, pp. 34631-34636.
Nash, Kevin T., et al., "The KISS 1 metastasis suppressor: mechanistic insights and clinical utility," Frontiers in Bioscience, vol. 11, 2006, pp. 647-659.
Lee, Jeong-Hyung, et al., "Identification of highly expressed genes in metastasis-suppressed chromosome 6/human malignant melanoma hybrid cells using subtractive hybridization and differential display," Int. J Cancer, vol. 71, Issue 6, 1997, pp. 1035-1044.
Roa, J., et al., "Hypothalamic expression of KiSS-1 system and gonadotropin-releasing effects of kisspeptin in different reproductive states of the female Rat," Endocrinology, vol. 147, Issue 6, 2006, pp. 2864-2878.
Stahl, P. Heinrich, et al., "Handbook of Pharmaceutical Salts for a review of pharmaceutically acceptable salts: Properties, Selection, and Use," Chapter 4, Wiley-VCH, 2002, 34 pages.
Rautio, J., "Prodrugs: design and clinical applications," Nature Reviews | Drug Discovery, vol. 7, Issue 3, 2008, pp. 255-270.
Stella, Valentino J., et al., "Prodrugs: Challenges and rewards," Springer, 2007.
Lu, Gui-shen, et al., "Improved Synthesis of 4-Alkoxybenzyl Alcohol Resin," J. Org. Chem, vol. 46, Issue 17, 1981, pp. 3433-3436.
Asami, Taiji, et al., "Design, Synthesis, and Biological Evaluation of Novel Investigational Nonapeptide KISS1R Agonists with Testosterone-Suppressive Activity," Journal of Medicinal Chemistry, vol. 56, Issue 21, 2013, pp. 8298-8307.
Decourt, C., et al., "A synthetic kisspeptin analog that triggers ovulation and advances puberty," Scientific Reports, vol. 6, Issue 1, 2016, pp. 1-10.
Beltramo, Massimiliano, et al., Rational Design of Triazololipopeptides Analogs of Kisspeptin Inducing a Long-Lasting Increase of Gonadotropins, Journal of Medicinal Chemistry, vol. 58, Issue 8, 2015, pp. 3459-3470.
Asami, Taiji, et al., "Serum stability of selected decapeptide agonists of KISS1R using pseudopeptides," Bioorganic & Medicinal Chemistry Letters, vol. 22, Issue 20, 2012, pp. 6391-6396.
Extended European Search Report dated Dec. 10, 2020 issued in EP Application No. 18828694.2, 12 pages.
Stafford LJ, Xia C, Ma W, Cai Y, Liu M. "Identification and characterization of mouse metastasis-suppressor KiSS1 and its G-protein-coupled receptor". Cancer Res. Oct. 1, 2002;62(19):5399-404.
Nash KT, Welch DR. The KISS1 metastasis suppressor: mechanistic insights and clinical utility. Front Biosci. Jan. 1, 2006; 11: 647-59. doi: 10.2741/1824.
Pruszyńska-Oszmałek E, Kołodziejski PA, Sassek M, Sliwowska JH. Kisspeptin-10 inhibits proliferation and regulates lipolysis and lipogenesis processes in 3T3-L1 cells and isolated rat adipocytes. Endocrine. Apr. 2017;56(1):54-64. doi: 10.1007/s12020-017-1248-y. Epub Feb. 13, 2017. PMID: 28194651.
Nikitina IL, Khoduleva YN, Masel AS, Bairamov AA, Shabanov PD. System of KISS-KISS1R: focus on peripheral signaling in androgen-dependent tissues in the experimentally induced model hypogonadotropic hypogonadism. Patol Fiziol Eksp Ter. Oct.-Dec. 2016 60(4):24-33. PMID: 29244919.
Gahete MD, Vázquez-Borrego MC, Martínez-Fuentes AJ, Tena-Sempere M, Castaño JP, Luque RM. Role of the Kiss1/Kiss1r system in the regulation of pituitary cell function. Mol Cell Endocrinol. Dec. 15, 2016; 438: 100-106. doi: 10.1016/j.mce.2016.07.039. Epub Jul. 29, 2016. PMID: 27477782.
Colledge WH. Transgenic mouse models to study Gpr54/kisspeptin physiology. Peptides. Jan. 2009;30(1):34-41. doi: 10.1016/j.peptides. 2008.05.006. Epub May 15, 2008. PMID: 18571287.
Seminara SB, Crowley WF Jr. Kisspeptin and GPR54: discovery of a novel pathway in reproduction. J Neuroendocrinol. Jun. 2008; 20(6): 727-31. doi: 10.1111/j.1365-2826.2008.01731.x. PMID: 18601695; PMCID: PMC2869294.
Ohkura S, Uenoyama Y, Yamada S, Homma T, Takase K, Inoue N, Maeda K, Tsukamura H. Physiological role of metastin/kisspeptin in regulating gonadotropin-releasing hormone (GnRH) secretion in female rats. Peptides. Jan. 2009;30(1):49-56. doi: 10.1016/j.peptides. 2008.08.004. Epub Aug. 19, 2008. PMID: 18775461.
B Umayal , S N Jayakody , N V Chandrasekharan , W Ss Wijesundera , C N Wijeyaratne Polycystic ovary syndrome (PCOS) and kisspeptin—A Sri Lankan study. J Postgrad Med. 1019 Jan.-Mar.; 65(1):18-23.
De Roux N. GnRH receptor and GPR54 inactivation in isolated gonadotropic deficiency. Best Pract Res Clin Endocrinol Metab. Dec. 2006;20(4):515-28.
Bry-Gauillard H, Trabado S, Bouligand J, Sarfati J, Francou B, Salenave S, Chanson P, Brailly-Tabard S, Guiochon-Mantel A, Young J. Congenital hypogonadotropic hypogonadism in females: clinical spectrum, evaluation and genetics. Ann Endocrinol (Paris). May 2010;71(3):158-62.
Noel SD, Kaiser UB. G protein-coupled receptors involved in GnRH regulation: molecular insights from human disease. Mol Cell Endocrinol. Oct. 22, 2011;346(1-2):91-101.
Tena-Sempere M. KISS-1 and reproduction: focus on its role in the metabolic regulation of fertility. Neuroendocrinology. 2006;83(5-6):275-81.
Castellano JM, Roa J, Luque RM, Dieguez C, Aguilar E, Pinilla L, Tena-Sempere M. KiSS-1/kisspeptins and the metabolic control of reproduction: physiologic roles and putative physiopathological implications. Peptides. Jan. 2009;30(1):139-45.
Seminara SB, Crowley WF Jr. Kisspeptin and GPR54: discovery of a novel pathway in reproduction. J Neuroendocrinol. Jun. 2008;20(6):727-31.
Jayasena CN, Dhillo WS. Kisspeptin offers a novel therapeutic target in reproduction. Curr Opin Investig Drugs. Apr. 2009;10(4):311-8.
Peptides: Basic determinants of reproductive functions. Celik O, Aydin S, Celik N, Yilmaz M. Peptides. Oct. 2015; 72: 34-43. doi: 10.1016/j.peptides.2015.05.016. Epub Jun. 12, 2015. PMID: 26074346 Review.
Continuous human metastin 45-54 infusion desensitizes G protein-coupled receptor 54-induced gonadotropin-releasing hormone release monitored indirectly in the juvenile male Rhesus monkey (Macaca mulatta): a finding with therapeutic implications. Seminara SB, Dipietro MJ, Ramaswamy S, Crowley WF Jr, Plant TM. Endocrinology. May 2006; 147(5): 2122-6. doi:10.1210/en.2005-1550. Epub Feb. 9, 2006. PMID: 16469799.
Kisspeptin and its receptor: new gatekeepers of puberty. Messager S. J Neuroendocrinol. Oct. 2005; 17(10): 687-8. doi:10.1111/j.1365-2826.2005.01357.x. PMID: 16159382.
Regulation of the neuroendocrine reproductive axis by kisspeptin-GPR54 signaling. Smith JT, Clifton DK, Steiner RA. Reproduction. Apr. 2006;131(4):623-30. doi: 10.1530/rep.1.00368.
Hiden U, Bilban M, Knöfler M, Desoye G. Kisspeptins and the placenta: regulation of trophoblast invasion. Rev Endocr Metab Disord. Mar. 2007;8(1):31-9.

* cited by examiner

PEPTIDE COMPOUND AND APPLICATION THEREOF, AND COMPOSITION CONTAINING PEPTIDE COMPOUND

This application is a division of U.S. patent application Ser. No. 16/628,586 filed on Jan. 3, 2020. U.S. Ser. No. 16/628,586 is a U.S. National Phase Application under 35 U.S.C. 371 of International Application No. PCT/CN2018/094618 filed on Jul. 5, 2018. This application claims the priority of Chinese patent application CN201710543383.0 filed on Jul. 5, 2017 and Chinese patent application CN201810725881.1 filed on Jul. 4, 2018. The content of said Chinese patent application is hereby incorporated by reference in its entirety.

FIELD OF INVENTION

The disclosure relates to a peptide compound and an application thereof, and a composition containing the peptide compound.

PRIOR ARTS

Kiss-1 gene is a novel type of gene that inhibit the metastasis of human melanoma discovered by Jeong-Hyung Lee et al. (Lee J H, et al. Journal of the national cancer institute, vol. 88 (23): 1731-1737 (1996)). Kiss-1 gene is located on human chromosome 1q32 and consists of four exons, two untranslated and two partially translated exons, which encodes a precursor polypeptide containing 145 amino acids. The precursor peptide is cleaved into 54 amino acid length Kisspeptin-54 (also known as metastin or transfer inhibitor), and can be further truncated to 14 [kisspeptin-14/metastin (40-54)], 13 [kisspeptin-13/metastin (41-54)], or 10 [kisspeptin-10/metastin (45-54)] amino acids. These truncations and precursors are collectively referred to as Kisspeptin (Kp) and are highly conserved in mammals (Kotanim, et. al. Journal of biological chemistry, vol. 276 (27): 34631-34636; Ohtaki T. et al., Nature Vol, 411(6837): 613-671 (2001)). The four kisspeptins all contain the same 10 amino acid residues, the C-terminal of which has arginine and amidated phenylalanine (RF-amide), but the N-terminal polypeptides differ in length. The C-terminal part of the kisspeptins is related to the efficient binding and activation of the receptors, and the activity of truncated peptides, for example Kisspeptin-10 and Kisspeptin-14 is 3-10 times higher than that of Kisspeptin-54. mRNA of the Kiss-1 is mainly expressed in human placenta and is also widely expressed in the whole central nervous system: the highest expression is in the shell, the higher expression is in caudate nucleus, globus pallidus, hypothalamus, nucleus accumbens and cerebellum, and the lower expression is in superior frontal gyms, amygdala, cingulate gyms, hippocampus, para hippocampal gyms, thalamus, substantia nigra, locus coeruleus and medulla oblongata, and the very low expression is in spinal cord.

At present, it is known that the receptor for these kisspeptins (Kiss1R) is a member of retinoic acid-inducible orphan G protein-coupled receptor family (namely GPR54 in rats and AXOR12 in humans). Kiss1R contains 398 amino acid residues and is related to the galanin receptor family, but it does not bind to galanin. Rat GPR54 is highly conserved in mammals and has 81% homology with human receptors and 85% homology with mice. The mRNA of human Kiss1R is expressed abundantly in placenta, pituitary, spinal cord and pancreas, and is expressed at a low level in other tissues including different parts of brain (thalamus, caudate nucleus, substantia nigra, hippocampus, amygdala, and cerebellum), stomach, small intestine, thymus, spleen, lung, testis, kidney and fetal liver. Kisspeptin and its receptors are distributed in brain and in various peripheral tissues and organs, including hypothalamus, aorta, ovary, prostate and placenta, and the receptors are also expressed in pituitary gland. Their functions include regulating reproductive function, affecting endocrine, and affecting the growth and metastasis of tumor cells.

The signal transmission between kisspeptin and Kiss1R (GPR54) is to activate phospholipase C(PLC) in the cell after the polypeptide binds with its receptor, and then hydrolyze phosphatidylinositol diphosphate (PIP2) to produce inositol triphosphate (IP3) and diacylglyceride (DAG), which promote the increasement of intracellular calcium ion, the realsing of arachidonic acid, the activation of protein kinase C(PKC), and the phosphorylation of the extracellular signal regulatory kinases (ERK1 and ERK2) and p38 mitotic activated protein kinase (MAPK), thus producing the biological effects. An important role of the signalling between Kisspeptin and Kiss1R is to start secreting gonadotropin-releasing hormone (GnRH) during puberty. The release of gonadotropin-releasing hormone is the behavior of the anterior pituitary gland, which also includes the release of luteinizing hormone, LH) and follicle stimulating hormone, FSH). Disruption of this signaling pathway will lead to insufficient GnRH release, resulting in hypogonadism in humans and rodents. Abnormal release or absence is the main cause of abnormal sexual reproduction for men and women. Studies have proved that GnRH analogue kisspeptin plays a role at hypothalamic level to stimulate GnRH release (U.S. Pat. No. 7,754,220). The input of kisspeptin can stimulate GnRH to release at all stages. The use of Kiss1R agonist is a method for preventing or treating hormone-related diseases for example prostate cancer, breast cancer, endometriosis, hysteromyoma, breast cancer before amenorrhea, central precocious puberty, sexual functional diseases, etc. It is also used in in vitro fertilization to induce ovulation and as a new generation of contraceptives.

The binding of the kisspeptin and Kiss1R (GPR54) has many functions, among which the inhibition of cell proliferation is an important one (Kotanim, et al., J. Biol. Chem. vol. 276: 34631-34636). Kiss1R agonist can inhibit cell proliferative diseases selected from the following disease groups: benign prostatic hyperplasia, prostate cancer, breast cancer, ovarian cancer, uterine cancer, cervical cancer, endometrial cancer, melanoma, pancreatic cancer, gastric cancer, renal cell cancer, esophageal cancer, bladder cancer, brain cancer, etc.

Kiss1 gene is initially named as Kiss1 metastasis inhibitory gene, which can manage tumor cell metastasis and has clinical value. The expression level of primary melanoma cell line expressing Kiss1 gene is negatively related to the metastatic potential of melanoma cell line. C8161 cells expressed Kiss1 gene, and lung metastasis was inhibited by more than 95% (Nash et al., The KISS1 metastasis suppressor: mechanistic insights and clinical utility, Front. Biosci. vol. 11, pp. 647-659 (2006)). Kisspeptin can reduce cell mobility and inhibit tumor cell metastasis by inducing excessive cell adhesion phenotype (Lee J H and Welch D R, Int. J. Cancer, vol. 71 (6): 1035-1044 (1997)). Metastin derivatives also have excellent biological activities (e.g., cancer cell metastasis inhibitory activity, cancer cell growth inhibitory activity, etc.) (U.S. Pat. Nos. 68,061B2, 7,625, 869B2, 8,361,986B2, 8,592,379B2). Kiss1R agonist inhibits tumor metastasis and migration, and affects the invasion of trophoblast cells, wherein said disease or disease state is selected from melanoma, pancreatic cancer, breast cancer, ovarian cancer, uterine cancer, cervical cancer, endometrial cancer, thyroid cancer, bladder cancer, esophageal squamous cell cancer, gastric cancer, liver cancer and other cancers.

Kiss1R (GPR54) is also highly expressed in the central nervous system (CNS) and the hippocampus region. It has been proved that, Kiss1R can reversibly enhance the synaptic transmission in hippocampal dentate gyms cells through mechanisms involving MAP kinases, which appears to be regulated by calcium-activated kinases and tyrosine kinases (Roa J, Hypothalamic expression of KiSS-1 system and gonadotropin-releasing effects of kisspeptin in different reproductive states of the female Rat. et. al. Endocrinology 147(6): 1624-1632, 2006). Studies have proved that injection of kisspeptin can enhance limbic brain activity and produce sexual stimulation. Therefore, kisspeptin can stimulate sexual desire in essence and is related to the feeling of sex appeal, romance and sexual excitement. Kiss1R agonist can enhance the erotic signals from brain and emotion, thus treating sexual dysfunction caused by psychological reasons.

Kisspeptin also has the function of affecting placental function, therefore, Kiss1R agonist is effective in treating the disease or disease state selected from: choriocarcinoma, invasive nevus, abortion, fetal hypoplasia, abnormal glucose metabolism, abnormal lipid metabolism, etc. (WO00/24890; WO01/75104 2; WO 02/85399).

Takeda company has disclosed kisspeptin analog TAK448 in patents CN 101341168B, U.S. Pat. No. 8,592,379B2, U.S. Pat. No. 8,765,909B2 and U.S. Pat. No. 9,778,871B2:

| Compound number | | Sequence |
|---|---|---|
| YA-156 | M10 [Palm-PEG8, G43, G44, D-Y45, Hyp46, des47, T49, azaGly51, R(Me)53, W54] | Palm-PEG8-Gly-Gly-(D-Tyr)-Hyp-Asn-Thr-Phe-azaGly-Leu-Arg(Me)-Trp-NH$_2$ |

The present disclosure also provides a use of the compound YA-156, the pharmaceutically acceptable salts, tautomers, crystal forms, solvates or prodrugs thereof in manufacturing a medicament for treating and/or preventing diseases related to kisspeptin receptors.

The present disclosure also provides a method for treating and/or preventing diseases related to kisspeptin receptors in a subject in need thereof, comprising administering an effective amount of the compound YA-156, the pharmaceutically acceptable salts thereof, a tautomers thereof, the crystal forms thereof, the solvates thereof or the prodrugs thereof Said diseases related to kisspeptin receptor such as hormone-related diseases, cell proliferative diseases, or diseases related to placental function.

Said hormone-related disease is, for example, prostate cancer, breast cancer (e.g., breast cancer before amenorrhea), endometriosis, hysteromyoma, central precocious puberty, estrogen receptor positive, sexual functional diseases (e.g., sexual dysfunction, sexual apathy), infertility, depression, or pregnancy.

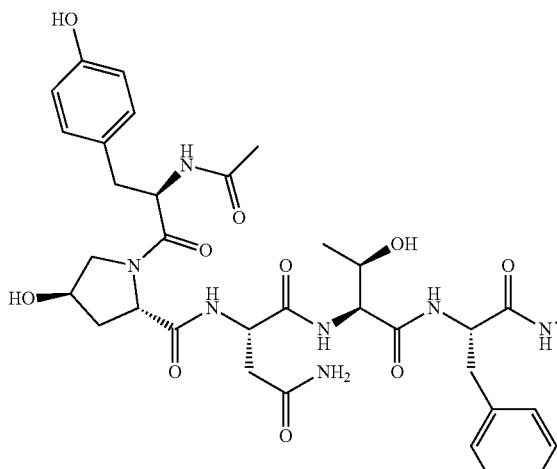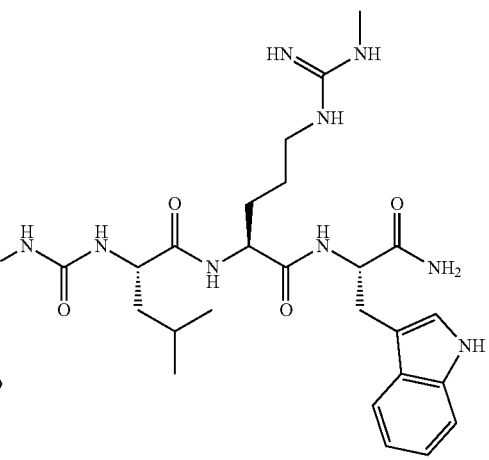

TAK448

CONTENTS OF THE PRESENT DISCLOSURE

The technical problem to be solved by the present disclosure is that the existing peptide compound has low stability and low activity to Kiss1R. Therefore, the present disclosure provides a peptide compound, an application thereof and a composition containing the peptide compound, which has better stability and activity to Kiss1R.

The present disclosure provides a peptide compound YA-156, a pharmaceutically acceptable salt thereof, a tautomer thereof, a solvate thereof, a crystal form thereof or a prodrug thereof:

Said cell proliferative disease is, for example, benign prostatic hyperplasia or cancer. Said cancer is, for example, prostate cancer, breast cancer, ovarian cancer, uterine cancer, cervical cancer, endometrial cancer, thyroid cancer, bladder cancer, liver cancer, melanoma, pancreatic cancer, gastric cancer, renal cell cancer, esophageal cancer (such as esophageal squamous cell cancer), bladder cancer or brain cancer.

Said diseases related to placental function is, for example, choriocarcinoma, invasive nevus, abortion, fetal hypoplasia, abnormal glucose metabolism or abnormal lipid metabolism.

On the basis of not violating common knowledge in the art, the above-mentioned preferred conditions can be combined arbitrarily to give various preferred examples of the present invention.

The reagents and raw materials used in the present disclosure are commercially available.

Unless otherwise specified, the terms used in the present invention have the following meanings:

The peptide molecules of the present invention are defined herein using conventional single letter codes for representing amino acids. The term "amino acid" includes water-soluble organic compounds having carboxyl (—COOH) and amino (—NH$_2$) groups attached to α-carbon atoms. The amino acid can be represented by the general formula R—CH(NH$_2$)COOH; said R group is a hydrogen or an organic group and determines the properties of any specific amino acid. Tetrahedral arrangement of four different groups around α-carbon atoms makes amino acids optically active. The two mirror image isomers are called L-isomer and D-isomer. Generally, only L-amino acids are components of proteins such as eukaryotic proteins.

Unless otherwise stated, the peptide molecules of the present disclosure comprise L-amino acids. When D-amino acid is present in the peptide molecule of the present disclosure, it is represented by a conventional single-letter amino acid code prefixed with "(D)".

As described, the molecule of the present disclosure may comprise or consist of a peptide sequence having "any D-amino acid" at a specific position. Said "any D-amino acid" includes any natural or unnatural (e.g., chemically modified) D-amino acid at a specific position in the sequence. Examples of natural D-amino acids are as follows: D-alanine; D-aspartic acid D-cysteine; D-glutamic acid; D-phenylalanine; D-glycine; D-histidine; D-isoleucine; D-lysine; D-leucine; D-methionine; D-asparagine; D-proline; D-glutamine; D-arginine; D-serine; D-threonine; D-valine; D-tryptophan; D-tyrosine. Examples of unnatural D-amino acids are as follows: naphthylalanine; D-pyridylalanine; D-tert-butylserine; D-ornithine; D-ε aminolysine; D-hyperarginine; D-α methylleucine and the substitution of halogens (e.g., F) for protons in these and other unnatural amino acids.

By forming peptide bonds, amino acids are combined to form short chains (peptides) or longer chains (polypeptides). It is known that proteins and/or peptides are composed of about 20 common amino acids with different mobile phase ratios, and their sequences determine the shape, properties and biological effects of proteins and/or peptides. Amino acid residues in the chain of such peptides or polypeptides are usually represented by their arrangement positions on the chain, and the first site (i.e., site 1) is designated as the amino acid at the N-terminus of the chain.

TABLE 1

Explanation of Amino Acid Abbreviations

| Abbreviation | Full name |
| --- | --- |
| Ala | Alanine |
| Cys | Cysteine |
| Asp | Aspartic acid |
| Glu | glutamate |
| Phe | Phenylalanine |
| Gly | glycine |
| His | histidine |
| Ile | Isoleucine |
| Lys | Lysine |
| Leu | leucine |
| Met | met |
| Asn | asparagine |
| Pro | proline |
| Gln | Glutamine |
| Arg | Arginine |
| Ser | Serine |
| Thr | Threonine |
| Val | val |
| Trp | Tryptophan |
| Tyr | tyr |
| D-Ala | D-alanine |
| D-Cys | D-cysteine |
| D-Asp | D-aspartic acid |
| D-Glu | D-glutamic acid |
| D-Phe | D-Phenylalanine |
| D-Gly | D-glycine |
| D-His | D-histidine |
| D-Ile | D-isoleucine |
| D-Lys | D-lysine |
| D-Leu | D-leucine |
| D-Met | D-methionine |
| D-Asn | D-asparagine |
| D-Pro | D-proline |
| D-Gln | D-glutamine |
| D-Arg | D-arginine |
| D-Ser | D-serine |
| D-Thr | D-threonine |
| D-Val | D-valine |
| D-Trp | D-tryptophan |

TABLE 1-continued

Explanation of Amino Acid Abbreviations

| Abbreviation | Full name |
| --- | --- |
| D-Tyr, DTyr | D-tyrosine |
| Ac | Acetyl |
| cyc | The amino group of the N- terminal amino acid and the carboxyl group of the C- terminal amino acid are condensed to form an amide bond to form a ring. |
| Hyp | Trans-4-hydroxyproline |
| azaGly, azaG | Azoglycine |
| Arg(Me), R(Me) | N omega-methyl arginine, |
| N-Me-Arg, N-MeArg, NMeArg, NMe-Arg | N alpha-methyl arginine, |
| αMePhe, α-Me-Phe, αMe-Phe, α-MePhe | Alpha-methyl phenylalanine, |
| NMePhe, N-Me-Phe, N-MePhe, NMe-Phe | N-methyl phenylalanine |
| N-Me-D-Phe, NMe-D-Phe | N-methyl-D-phenylalanine |
| 1Nal, Nal1, Nal-1, 1-Nal | 1-naphthylalanine, |
| 2Nal, Nal2, Nal-2, 2-Nal | 2-naphthylalanine, |
| 4Pal, 4-Pal | 4-pyridylalanine, |

TABLE 1-continued

| Explanation of Amino Acid Abbreviations | |
|---|---|
| Abbreviation | Full name |
| Phe(4-F) | 4-fluorophenylalanine |
| αMeTyr, αMe-Tyr | Alpha-methyl tyrosine, |
| ψ(CH2NH)51 | The —CONH— bond between the 51st amino acid and the 52nd amino acid is replaced by the —CH$_2$NH— bond. |
| Ava | Delta-amyl acid, |
| Aib | Alpha-methyl alanine, |
| Sar | N-methylglycine, sarcosine |
| Chg | L-α-alpha-cyclohexylglycine, |
| Dap(Dnp) | N'-(2,4-dinitrophenyl)-L-2,3-diaminopropionic acid, |
| D-Phe(2,4-diCl), D-Phe(2,4-DiCl) | 2,4-dichloro-D-phenylalanine |
| D-2Fua, 3-(2-furyl)-D-Ala, 3-(2-furyl)-D-Alanine | 3-(2-furyl)-D-alanine, |
| Pro(5Ph), Pro(5-phenyl) | (2S,5R)-5-phenylpyrrolidine-2-carboxylic acid |
| Thz | 4-thioproline |
| Phe(3-Cl) | 3-chlorophenylalanine |
| Bta | 3-(3-benzothiophene) alanine |

TABLE 1-continued

Explanation of Amino Acid Abbreviations

| Abbreviation | Full name |
| --- | --- |
| HoPhe, HomoPhe | High phenylalanine (α-amino acid) |
| Phe(4-tBu) | 4-tert-butylphenylalanine |
| HoSer, HomoSer | Homoserine (α-amino acid) |
| 2Pal, 2-Pal | 2-pyridylalanine, |

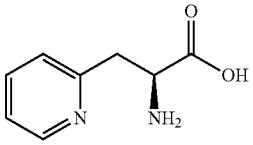 [SMILES: N[C@@H](Cc1ccccn1)C(=O)O]

| | |
| --- | --- |
| 3Pal, 3-Pal | 3-pyridylalanine, |

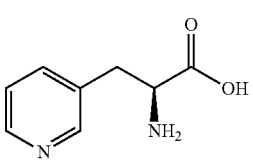 [SMILES: N[C@@H](Cc1cccnc1)C(=O)O]

| | |
| --- | --- |
| Phe(4-Cl) | 4-chlorophenylalanine |
| Tyr(Me) | O-methyl tyrosine, |

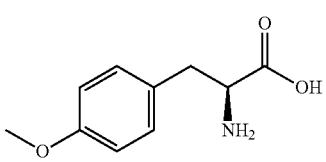

| | |
| --- | --- |
| Phe(4-Me) | 4-Methylphenylalanine |
| Cbz | carbobenzoxy- |
| Pro(di-F), Pro(diF), DifluoroPro, DiFluorPro | 4,4-difluoroproline |
| BetaAla, Beta-Ala | Beta-alanine |
| N-Me-Ala, NMe-Ala, NMeAla, N-MeAla | N-methyl alanine |
| N-Me-D-Ala, NMe-D-Ala, NMeD-Ala | N-methyl-D-alanine |
| N-Me-Leu, NMe-Leu, NMeLeu | N-methylleucine |
| N-Me-D-Leu, NMe-D-Leu, NMeD-Leu | N-methyl-D-leucine |
| Pro(4-NH$_2$), (4-aminoPro) | (2S,4R)-4-aminopyrrolidine-2-carboxylic acid |
| Thi | 3-(2-thienyl)-alanine |
| S-Pip | S-high proline, (S)-piperidine-2-formic acid |
| BetaHoLeu, BetaHomoLeu | Beta-homoleucine |
| HoLeu, HomoLeu | Homoleucine (α-amino acid) |
| D-HoLeu, D-HomoLeu | D-homoleucine (α-amino acid) |
| N-Me-HoLeu, N-Me-HomoLeu, NMe-HomoLeu | N-methyl homoleucine (α-amino acid) |
| N-Me-D-HoLeu, N-Me-D-HomoLeu, NMe-D-HomoLeu | D-N-methyl homoleucine (α-amino acid) |
| Nle | N-leucine |
| Cha | 3-cyclohexylalanine |
| Sta | (3S,4S)-4-amino-3-hydroxy-6-methylheptanoic acid |
| stapled | Two olefin groups in the same peptide undergo olefin metathesis reaction to form a ring. |
| X | (S)-2-amino-2-methyl-6-heptenoic acid |
| BetaPhe | Beta-phenylalanine |
| BataHoPhe, BetaHomoPhe | Beta-homophenylalanine |
| Phe(2-Br) | 2-bromophenylalanine |
| Phe(pentaF) | Pentafluorophenylalanine |
| Phe(4-CF3) | (4-trifluoromethyl)-phenylalanine |
| Bpa | (4-benzoyl)-phenylalanine |

TABLE 1-continued

Explanation of Amino Acid Abbreviations

| Abbreviation | Full name |
| --- | --- |
| Ala(dip) | 3,3-diphenyl alanine |
| NAsn | 2-((2-amino-2-oxoethyl)amino)acetic acid, |
| NLeu | N-(2-methylpropyl) glycine |
| NPhe | N-benzyl glycine |
| Phe(4-I) | 4-iodophenylalanine |
| 2Fua | 3-(2-furyl)-alanine |
| ACPA | 1-aminomethyl cyclopropylformic acid |
| PEG4 | 1-amino-3,6,9,12-tetraoxa-pentadec-15-acid, |
| PEG5 | 1-amino-3,6,9,12,15-pentaoxa-octadecyl-18-acid, |
| PEG8 | 1-amino-3,6,9,12,15,18,21,24-octaoxa-27C-27-acid, |
| PEG12 | 1-amino-3,6,9,12,15,18,21,24,27,30,33,36-dodecaoxa-39 carbon-39-acid, |
| ACPO | 3-Amino-1-Carboxymethyl-Pyridine-2-one |
| Aze | (S)-acridine-2-carboxylic acid |
| Bip | L-4,4'-biphenylalanine |
| Ac-Lys | |
| Palm, Palmitoyl | Palmitoyl |
| D-Phe(4-F) | D-4-fluorophenylalanine |
| A6c | 1-aminocyclohexyl formic acid |
| azaPro | Pyrazole alkane-1 formic acid, |
| D-Phe(4-Cl) | D-4-chlorophenylalanine |
| D-Phe(3-Cl) | D-3-chlorophenylalanine |
| Tic | L-1,2,3,4-tetrahydroisoquinoline-3-carboxylic acid |
| Ind | L-indoline-2-carboxylic acid |
| R-Pip, (R)-Pip, HoPro, HomoPro | R-homoproline,(R)-piperidine-2-formic acid |

TABLE 1-continued

Explanation of Amino Acid Abbreviations

| Abbreviation | Full name |
| --- | --- |
| S-Pip, (S)-Pip | S-homoproline,(S)-piperidine-2-formic acid |
| L-Pip | L-homoproline |
| Oic | L-octahydroindole-2-carboxylic acid |
| azaTic | 3,4-dihydrophthalazine-2(1H)-formic acid |
| N-Me-A6c, NMe-A6c, MeA6c | (1-methylamino)-cyclohexyl formic acid |
| D-Tic | D-1,2,3,4-tetrahydroisoquinoline-3-carboxylic acid |
| Phe(4-amidino), 4-(amidino)phenylalanine | 4-amidinophenylalanine |
| Phe(4-Pyrazol), Phe(4-Pyra),(S)-3-(4-(1H-pyrazol-1-yl)phenyl)-2-aminopropanoic acid | [4-(1H-pyrazol-1-yl)] phenylalanine |
| Aza-N-Me-Gly, azaNMeGly, aza-NMeGly | Aza-(N-methylglycine) |
| 1H-1,2,3-triazol-4-yl | Carboxyl-terminated —$CONH_2$ was substituted with 1H-1,2,3-triazol-4-yl |
| 2H-tetrazol-5-yl | Carboxyl-terminated —$CONH_2$ was substituted with 2H-tetrazole-5-yl |
| ψ(NHCO)51 | The —CONH— bond between amino acids 51 and 52 was replaced by —NHCO— bond. |
| ψ(NHCS)51 | The —CONH— bond between amino acids 51 and 52 was replaced by —NHCS— bond. |
| ψ(NH—CO—NH)51 | The —CONH— bond between amino acids 51 and 52 was replaced by —NH—CO—NH— bond. |
| Biotin | D-biotin, vitamin H |
| OEG | 2-(2-(2-aminoethoxy)ethoxy)acetic acid |
| | $(H_2N{\frown}{\frown}O)_2{\frown}{\frown}OH$ |
| azaPhe | Azaphenylalanine,1-benzylhydrazine-1 formic acid |
| cycloLeu | 1-aminocyclopentyl formic acid |
| BetaHoAla, BetaHomoAla | Beta-homoalanine |
| Cba | Beta-cyclobutylalanine, |
| Hexanoyl | Hexanoyl |
| Nonanoyl | Nonyl |
| Dodecanoyl | Dodecanoyl |
| C18 diacid | 1,18-octadecanedioic acid |
| Maleimide | Maleimide/Maleimide |
| Ahx | 6-aminocaproic acid |
| 3-[(1-methylpyridinium)-3-yl] alanine,(S)-3-(2-Amino-2-carboxyethyl)-1-methylpyridonium | |
| Alg | |

TABLE 1-continued

Explanation of Amino Acid Abbreviations

| Abbreviation | Full name |
|---|---|
| Deg | 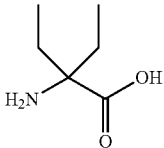 |
| AlphaMeLeu | 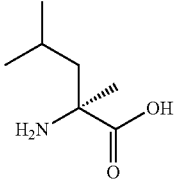 |
| Cpa | 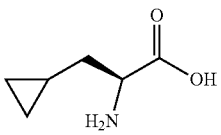 |
| ACBC | 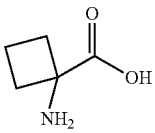 |
| Cpg | 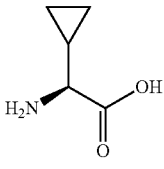 |
| morpholino cyclic amino acid | 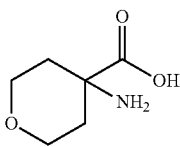 |
| beta-(thiazoly-4-yl)-L-Ala | 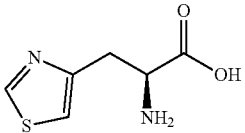 [SMILES: N[C@@H](Cc1cscn1)C(=O)O] |

The term "pharmaceutically acceptable salt" refers to a pharmaceutically acceptable organic or inorganic salt. Exemplary acid salts include, but are not limited to, sulfate, citrate, acetate, oxalate, chloride, bromide, iodide, nitrate, bisulfate, phosphate, acid phosphate, isonicotinic acid salt, lactate, salicylate, acid citrate, tartrate, oleate, tannate, pantothenate, hydrogen tartrate, ascorbate, succinate, maleate, fumarate, gluconate, glucuronic acid, gluconate, formate, benzoate, Glutamate, methanesulfonate, ethane sulfonate, benzenesulfonate, p-toluenesulfonate and pamoate (i.e., 1-1-methylene-bis (2-hydroxy -3-naphthalate)). The compound used in the present disclosure can form pharmaceutically acceptable salts with various amino acids. Suitable alkali salts include, but are not limited to, aluminum salts, calcium salts, lithium salts, magnesium salts, potassium salts, sodium salts, zinc salts, bismuth and diethanolamine salts. See Handbook of Pharmaceutical Salts for a review of pharmaceutically acceptable salts: Properties, Selection, and Use (P. Heinrich Stahl and Camille G. Wermuth, ed., Wiley-VCH, 2002).

The term "crystal form" refers to one or more crystal structures formed by different arrangement of molecules in lattice space during crystallization.

The term "solvate" is a crystalline form that contains, in addition to active molecules, one or more solvent molecules incorporated into the crystalline structure. The solvate may include a stoichiometric amount or a non-stoichiometric amount of solvent, and solvent molecules in the solvent may exist in an ordered or non-ordered arrangement. Solvents containing non-stoichiometric amounts of solvent molecules can be obtained by the solvate losing at least some (but not all) of the solvent molecules. In a particular embodiment, a solvate is a hydrate, meaning that the crystalline form of the compound may include water molecules.

The term "prodrug" refers to a derivative of a compound containing a bioreactive functional group such that under biological conditions (in vitro or in vivo), the bioreactive functional group can be cleaved from the compound or otherwise react to provide the compound. In general, prodrugs are inactive, or at least less active than the compound itself, so that their activity cannot be exerted until the compound is cleaved from the bioreaction functional group. The bioreaction functional group can be hydrolyzed or oxidized under biological conditions to provide the compound. For example, the prodrug may contain a biohydrolyzable group, and examples of biohydrolyzable groups include, but are not limited to, biohydrolyzable phosphates, biohydrolyzable esters, biohydrolyzable amides, biohydrolyzable carbonates, biohydrolyzable carbamates, and biohydrolyzable ureides. For the summary of prodrugs, see, for example, J. Rautio et al., nature reviews drug discovery (2008) 7,255-270 and prodrugs: Challenges and rewards (v. stella et al. ed., springer, 2007).

The term "alkyl" refers to a saturated linear or branched monovalent hydrocarbon group having one to eighteen carbon atoms (e.g., C1-C6 alkyl, also e.g., C1-C4 alkyl). Examples of alkyl include, but are not limited to, methyl, ethyl, 1-propyl, 2-propyl, 1-butyl, 2-methyl -1-butyl, 2-butyl, 2-methyl -2-propyl, 1-pentyl, 2-pentyl, 3-pentyl, 2-methyl -2-butyl, 3-methyl -2-butyl, 3-methyl -1-butyl, 2-methyl -1-butyl, 1-hexyl, 2-hexyl, 3-hexyl, 2-methyl -2-pentyl, 3-methyl -2-pentyl, 4-methyl-2-pentyl, 3-methyl -3-pentyl, 2-methyl -3-pentyl, 2,3-dimethyl -2-butyl, 3,3-dimethyl-2-butyl, 1-heptyl, 1-octyl.

The positive and progressive effect of the present dissclosure is that the compound of the present disclsure has better stability and better activity to Kiss1R.

DETAILED DESCRIPTION OF THE PREFERRED EMBODIMENT

The following embodiments further illustrate the present disclosure, but the present disclosure is not limited thereto. The conditions of the experimental methods that didn't specified by the following embodiments were selected according to conventional methods and conditions, or according to the commercial instructions.

The peptide compounds of the present disclosure were all synthesized according to Lu et al (1981) *J. Org. Chem.* 46, 3433 and Fmoc-polyamide solid phase peptide synthesis method disclosed in its references. 9-fluorenylmethoxycarbonyl (Fmoc) group is used to provide a temporary protection for N-amino. Repeated removal of the highly alkali labile protecting group is performed using N,N-dimethylformamide containing 20% piperidine. The side chain functional groups can be protected by their butyl ethers (in the case of serine, threonine and tyrosine), butyl esters (in the case of glutamic acid and aspartic acid), butyl oxycarboxyl derivatives (in the case of lysine and histidine), trityl derivatives (in the case of asparagine and glutamine) and 4-methoxy-2,3,6-trimethylbenzenesulfonyl derivatives (in the case of arginine). When the C-terminal residue is glutamine or asparagine, a 4,4'-dimethoxybenzhydryl group is used to protect the side chain amino functional group. The solid phase carrier is based on a polydimethyl-acrylamide polymer composed of three monomers of dimethylacrylamide (main chain monomer), diallylethylenediamine (crosslinking agent) and acryloyl sarcosinate methyl ester (functionalizing reagent). The peptide-resin cleavable connecter used herein is the acid unstable 4-hydroxymethyl-phenoxyacetic acid derivative. Except for asparagine and glutamine, all amino acid derivatives were added as their prefabricated symmetric anhydride derivatives, while asparagine and glutamine were added using reverse N,N-dicyclohexylcarbodiimide/1-hydroxybenzotriazole mediated coupling method. All coupling and deprotection reactions were monitored using ninhydrin, trinitrobenzenesulfonic acid or isotin detection methods. When the synthesis was completed, the peptide was cleaved from the resin carrier, and at the same time, the protecting group of the side chain was removed by treatment with 95% trifluoroacetic acid containing 50% scavenger mixture. Scavengers that commonly used were ethanedithiol, phenol, anisole and water, and the accurate selection depended on the amino acid composition of the synthesized peptide. Trifluoroacetic acid was removed by vacuum evaporation, followed by grinding with diethyl ether to provide crude peptide. Any scavenger present was removed by a simple extraction step, wherein the crude peptide free of scavenger was provided by lyophilizing the aqueous phase. Reagents for peptide synthesis can be generally purchased from calbiochem-novabiochem (UK) ltd., Nottingham NG7 2QJ, uk. Purification can be achieved by any one or combination of techniques such as volume exclusion chromatography, ion exchange chromatography, and (mainly) reverse phase high performance liquid chromatography. Peptide analysis can be performed using thin layer chromatography, reversed-phase high performance liquid chromatography, amino acid analysis after acid hydrolysis, and rapid atom bombardment (FAB) mass spectrometry.

At the same time, the peptide compounds of the present disclosure can also be synthesized by liquid phase method well known to those skilled in the chemical and biochemical fields.

After synthesis, the peptide sequence of the active agent of the present disclosure can be purified using methods known in the art, such as HPLC and chromatography.

Preparation Embodiment 1 Preparation of Fmoc-Phe-Aza-Leu-OH (Special Compound Included in YA-3)

(2-(((9H-fluorene-9-yl) methoxy) carbonyl-L-phenylalaninyl-2-hydrazino-1-carbonyl-L-leucine)

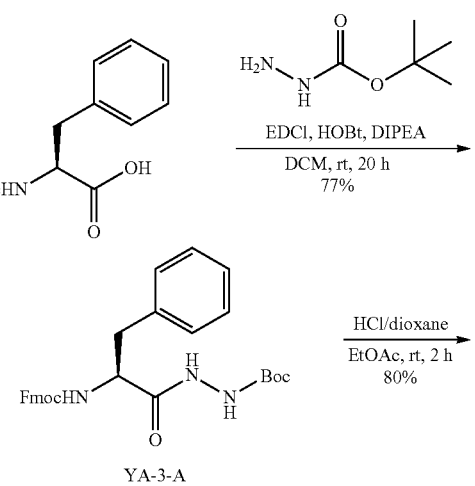

YA-3-A

-continued

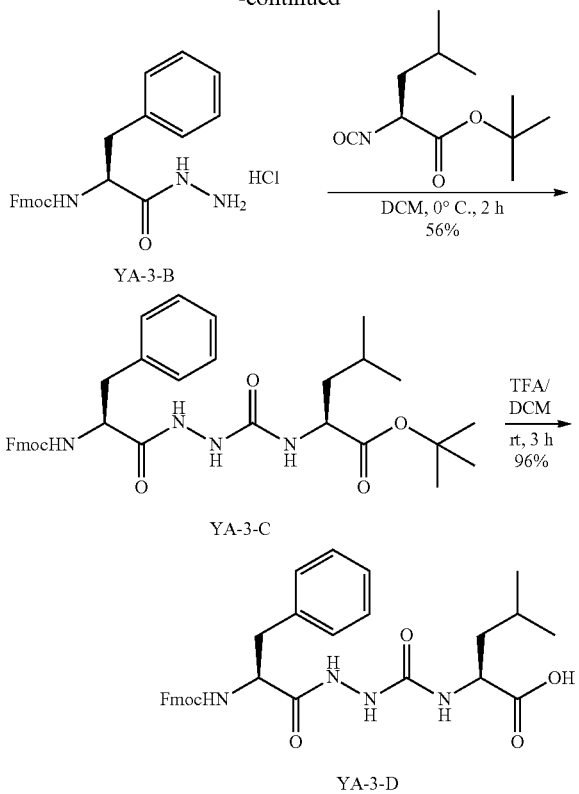

YA-3-B

YA-3-C

YA-3-D

Step 1: (S)-2-(2-((9H-fluorene-9-yl) methoxy) carbonylamino)-3-phenylpropionyl) tert-butyl hydrazinocarboxylate (compound YA-3-A)

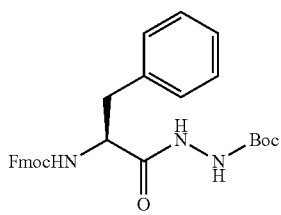

(S)-2-((9 hydrogen-fluorene-9-yl) methoxy) carbonylamino)-3-phenylalanine (10 g, 25.8 mmol), tert-butyl hydrazine formate (3.41 g, 25.8 mmol), HOBt (5.23 g, 38.7 mmol) and 1-(3-dimethylaminopropyl)-3-ethylcarbodiimide hydrochloride (7.42 g, 38.7 mmol) were dissolved in dichloromethane (250 mL), and after stirring at room temperature for 10 minutes, diisopropylethylamine (6.67 g, 51.6 mmol) was added. The mixture was stirred at room temperature for 20 hours and then concentrated. 300 mL of petroleum ether and 30 mL of water were added to the residue, stirred at room temperature for 10 minutes, filtered, the solid was washed with mixed solution EA:PE=1:5 (180 mL), and the filter cake was dried to give the captioned compound (10 g, 77%) as a white solid. LCMS (ESI) [M−99]+=402.0.

Step 2: (S)-2-(2((9H-fluorene-9-yl) methoxy) carbonylamino)-3-phenylpropionyl) hydrazine hydrochloride (compound YA-3-B)

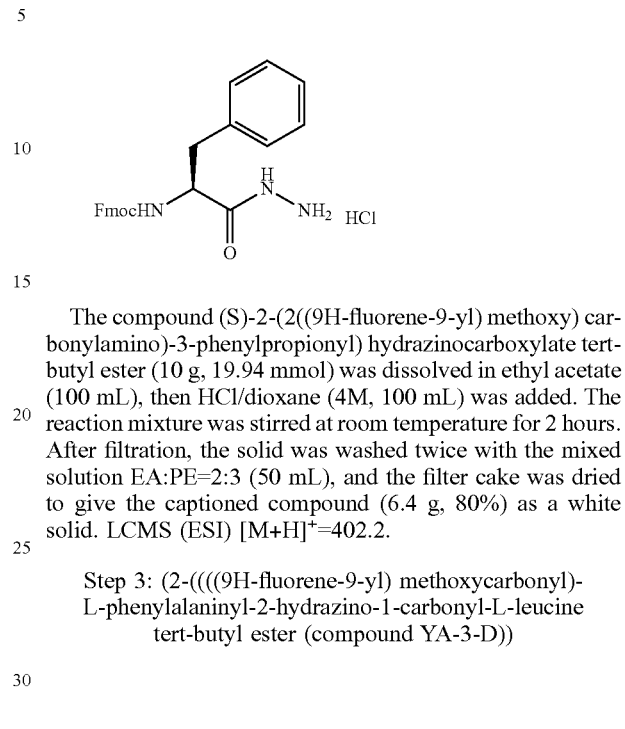

The compound (S)-2-(2((9H-fluorene-9-yl) methoxy) carbonylamino)-3-phenylpropionyl) hydrazinocarboxylate tert-butyl ester (10 g, 19.94 mmol) was dissolved in ethyl acetate (100 mL), then HCl/dioxane (4M, 100 mL) was added. The reaction mixture was stirred at room temperature for 2 hours. After filtration, the solid was washed twice with the mixed solution EA:PE=2:3 (50 mL), and the filter cake was dried to give the captioned compound (6.4 g, 80%) as a white solid. LCMS (ESI) [M+H]+=402.2.

Step 3: (2-((((9H-fluorene-9-yl) methoxycarbonyl)-L-phenylalaninyl-2-hydrazino-1-carbonyl-L-leucine tert-butyl ester (compound YA-3-D))

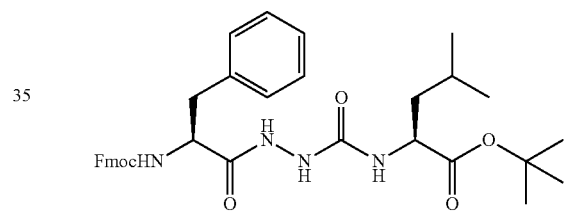

The hydrochloride of compound (S)-2-(2-((9 hydrogen-fluorene-9-yl) methoxy) carbonylamino)-3-phenylpropionyl) hydrazine (6.4 g, 16 mmol) and tert-butyl (S)-2-isocyanate-4-methylpentanoate (4.42 g, 20.7 mmol) were dissolved in methylene chloride (200 mL), and the reaction mixture was stirred at 0° C. for 2 hours. The reaction mixture was concentrated, and the crude product was isolated and purified by high-speed chromatography (petroleum ether/ethyl acetate=1/3) to give the captioned compound (5.5 g, 56%) as a white solid. LCMS (ESI) [M−55]+=559.3.

Step 4: (2-((((9H-fluorene-9-yl) methoxycarbonyl-L-phenylalaninyl-2-hydrazino-1-carbonyl-L-leucine) (compound YA-3-D))

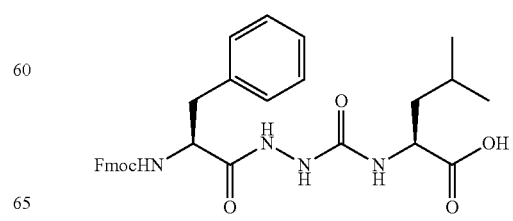

The compound (2-((((9 hydrogen-fluorene-9-yl) methoxy) carbonyl)-L-phenylalaninyl-2-hydrazino-1-carbonyl-L-leucine tert-butyl ester (5.5 g, 8.95 mmol) was dissolved in dichloromethane (20 mL), trifluoroacetic acid (20 mL) was added, and the reaction mixture was stirred at room temperature for 3 hours. The reaction mixture was concentrated, and the resulting residue was isolated and purified by high-speed chromatography (dichloromethane/methanol=4/1) to give the captioned compound (4.8 g, 96%) as a white solid. LCMS (ESI) $[M+H]^+$=559.2. $^1$H NMR (400 MHz, DMSO-d6) δ 8.34 (s, 1H), 8.23 (s, 1H), 7.99 (s, 1H), 7.88 (d, J=7.6 Hz, 2H), 7.75 (d, J=7.6 Hz, 1H), 7.64 (q, J=11.6 Hz, 2H), 7.42-7.25 (m, 9H), 7.20 (d, J=7.2 Hz, 1H), 4.16-4.11 (m, 3H), 3.02 (d, J=10.0 Hz, 1H), 2.84 (d, J=10.8 Hz, 1H), 2.51 (s, 2H), 1.63 (s, 1H), 1.48-1.46 (m, 2H), 0.87-0.82 (m, 6H).

Embodiment 1

Preparation of Ac-(D-Tyr)-Hyp-Asn-Thr-Phe-azaGly-Leu-Arg (Me)-trp-NH$_2$

Step 1: 5.0 g of commercially available Rink Amide MBHA resin (0.5 mmol/g) was swollen in DMF, and the resin was treated with 20 mL 20% piperidine/DMF for 20 minutes to remove Fmoc, repeated twice. The obtained resin was washed with DMF, 20 mL DMF solution of Fmoc-Trp (Boc)-OH (4.0 g, 7.5 mmol), HATU (2.85 g, 7.5 mmol) and HOAt (1.04 g, 7.5 mmol) was added, then DIPEA (2.6 mL, 15 mmol) was added, the resin was treated at room temperature for 40 minutes, and the resin was washed with DMF to give Fmoc-Trp(Boc)-Rink Amide MBHA resin. The resin was treated with 20 ml of 20% piperidine/DMF for 20 minutes to remove Fmoc, repeated twice. The resin was washed with DMF, and a solution of Fmoc-Arg (Me, Pbf)-OH (2.08 g, 3.0 mmol) in 20 mL DMF, DIC (945 mg, 7.5 mmol) and HOBt (1.01 g, 7.5 mmol) were added to react overnight at room temperature. The resin was treated with 20 mL 20% piperidine/DMF for 20 minutes to remove Fmoc, repeated twice. The resin was washed with DMF to give Arg (Me, Pbf)-Trp (Boc)-Rink amide MBHA resin. The obtained resin was added with 15 mL DMF solution of Fmoc-Phe-azaGly-Leu-OH (1.68 g, 3.0 mmol), DIC (945 mg, 7.5 mmol) and HOBt (1.01 g, 7.5 mmol), and reacted overnight at room temperature. The resin was treated with 20 mL 20% piperidine/DMF for 20 minutes to remove Fmoc, repeated twice. The resin was washed with DMF to give Phe-azaGly-Leu-Arg (Me, Pbf)-Trp (Boc)-Rink Amide MBHA resin. In a similar manner, amino acids such as Thr(tBu), Asn(Trt), Hyp(tBu), D-Tyr(tBu) and the like were sequentially introduced to give NH$_2$-D-Tyr(tBu)-Hyp(tBu)-Asn(Trt)-Thr(tBu)-Phe-azaGly-Leu-Arg(Me, Pbf)-Trp (Boc)-Rink Amide MBHA resin. The mixture was washed with DMF, then 10 mL DMF solution of AcOH (44 ml, 7.5 mmol), DIC (945 mg, 7.5 mmol) and HOBt (1.01 g, 7.5 mmol) were added, the reaction was performed overnight at room temperature to introduce Ac group. The resin was washed with DMF, DCM, methanol and methyl tert-butyl ether, and then drained to finally give 8.6 g of Ac-D-Tyr (tBu)-Hyp(tBu)- Asn(Trt)-Thr(tBu)-Phe-azaGly-Leu-Arg (Me, Pbf)-Trp(Boc)-Rink Amide MBHA resin.

Step 2: The dried resin was added into 85 mL of TFA/TIS/EDT/H$_2$O (94/2/2/2) solution, the mixture was stirred for 2 hours, filtered to remove the resin, and the resin was washed with 20 mL of TFA/TIS/EDT/H$_2$O (94/2/2/2) solution. The filtrates were pooled, cold diethyl ether (1000 mL) was added to the filtrate, and the resulting mixture was centrifuged at 3000 rpm for 3 minutes to remove the supernatant, and the solid was washed twice with diethyl ether and drained.

Step 3: The obtained crude precipitate was dissolved with DMF, and then linear gradient elution (17 minutes) was performed at a flow rate of 25 mL/minute. Eluent AB: 79/21-69/31 using: eluent A: 0.05% TFA aqueous solution, eluent B: 0.05% TFA acetonitrile solution was applied on a preparative HPLC using Phenomenex Gemini 10 µ, 110 Å column (21.2×250 mm). The fractions containing the product were collected and lyophilized to give 1.2 g of trifluoroacetate, and 1.0 g of acetate was obtained by salt conversion, all of which were white solids.

Embodiment 2

Preparation of Palm-PEG8-Gly-Gly-(D-Tyr)-Hyp-Asn-Thr-Phe-azaGly-Leu-Arg(Me)-Trp-NH$_2$ (Compound YA-156)

Step 1: 0.26 g of commercially available Rink Amide MBHA resin (0.5 mmol/g) was swelled in DMF to give NH2-Gly-Gly-D-Tyr(tBu)-Hyp(tBu)-Asn(Trt)-Thr(tBu)-Phe-azaGly-Leu-Arg(Me,Pbf)-Trp(Boc)-Rink Amide resin according to Embodiment 1. The resin was washed with DMF, 10 mL DMF solution of Fmoc-PEG8-CH$_2$CH$_2$—COOH (126 mg, 0.19 mmol), HBTU (227 mg, 0.6 mmol), HOBt (81 mg, 0.6 mmol) were added, then DIPEA (209 µL, 1.2 mmol) was added, and treated at room temperature for 40 minutes, and added with PEG 8. The resin was treated with 5 ml of 20% piperidine/DMF for 20 minutes to remove Fmoc, repeated twice. The obtained resin was washed with DMF, 10 mL DMF solution of Palm Acid (61.5 mg, 0.24 mmol), HBTU (227 mg, 0.6 mmol), HOBt (81 mg, 0.6 mmol) were added, and then DIPEA (209 µL, 1.2 mmol) was added and treated at room temperature for 40 minutes. Palm-PEG8-Gly-Gly-D-Tyr-Asn-Trp-Asn-Ser-Tic-Gly-Leu-Arg-Phe-MBHA was obtained. The resin was washed with DMF, DCM, methanol and methyl tert-butyl ether, and then drained to give Ac-PEG4- D-Tyr(tBu)-Hyp(tBu)-Asn(Trt)-Thr(tBu)-Phe-azaGly-Leu-Arg(Me,Pbf)-Trp(Boc)-Rinkamide MBHA resin.

Step 2: The dried resin was added to 10 mL of TFA/TIS/H$_2$O (95/2.5/2.5) solution, the mixture was stirred for 2 hours, the resin was removed by filtration, and the resin was washed with 2 mL of TFA/TIS/H$_2$O (95/2.5/2.5) solution. The filtrates were combined, and ice methyl tert-butyl ether (70 mL) was added to the filtrate. The resulting mixture was centrifuged at 3000 rpm for 3 minutes, and the solid was washed twice with ice ethyl ether and drained. The obtained precipitate was dissolved in DMF and then eluted with a linear concentration gradient (10 minutes) at a flow rate of 25 mL/minute, and eluent AB: 47/53-37/63, using: eluent A: 0.05% TFA aqueous solution, eluent B: 0.05% TFA acetonitrile solution, was applied on a HPLC using Xtimate C18, 10 µm, 120 column (20×250 mm). The fractions containing the product were collected and lyophilized to give 20.4 mg of white solid.

The polypeptides prepared in the above the embodiments and the polypeptides prepared with reference to the above the embodiments were shown in Table 2 below. Table 2 also describes the purity analysis conditions, retention time, characterization data and effect data of each polypeptide (which were measured according to the method of effect Embodiment 1)

TABLE 2

| Compound number | | Sequence | Mw (obs.) [M + 2H]²⁺/2 | Mw (cal.) | Rt (min.) HPLC | HPLC purity analysis conditions | Preliminary measurement data (GPR54 EC50, nM) |
|---|---|---|---|---|---|---|---|
| YA-156 | M10 [Palm-PEG8, G43, G44, D-Y45, Hyp46, des47, T49, azaGly51, R(Me)53, W54] | Palm-PEG8-Gly-Gly-(D-Tyr)-Hyp-Asn-Thr-Phe-azaGly-Leu-Arg(Me)-Trp-NH$_2$ | 980.3 | 1958.32 | 9.28 | H | 0.045 |

The HPLC purity analysis conditions in above Table 2 are as follows:

Condition A: Elution A/B=95/5–35/65
Mobile phase: A: Water (0.01% TFA), B: ACN (0.01% TFA)
Mobile phase ratio: 5% B within 0-3 min, linear gradient elution 5-65% B within 20 min
Velocity: 1.2 ml/min
Column: Eclipse XDB-C18, 4.6*150 mm, 5 μm
Box temperature: 40° C.
Condition B: Elution A/B=95/5–35/65
Mobile phase: A: Water (0.01% TFA), B: ACN(0.01% TFA)
Mobile phase ratio: 5% B within 0-3 min, linear gradient elution 5-65% B within 20 min
Velocity: 1.0 ml/min
Column: AGLIENT ZORBAX Eclipse XDB, C18, 4.6*150 mm, 5 μm
Temperature: 40° C.
Condition C: Elution A/B=95/5–35/65
Mobile phase: A: Water (0.01% TFA), B: ACN (0.01% TFA)
Mobile phase ratio: 5% B within 0-3 min, linear gradient elution 5-65% B within 20 min
Velocity: 1.0 ml/min
Column: SunFire C18, 4.6*150 mm, 3.5 μm
Temperature: 40° C.
Condition D: Elution A/B=95/5–35/65
Mobile phase: A: Water (0.05% TFA), B: ACN (0.05% TFA)
Mobile phase ratio: 5% B within 0-3 min, linear gradient elution 5-65% B within 20 min
Velocity: 1.2 ml/min
Column: Eclipse XDB-C18, 4.6*150 mm, 5 μm
Condition E: Elution A/B=85/15–25/75
Mobile phase: A: Water (0.01% TFA), B: ACN (0.01% TFA)
Mobile phase ratio: 15% B within 0-3 min, linear gradient elution 15-75% B within 20 min
Velocity: 1.0 ml/min
Column: SunFire C18, 4.6*150 mm, 3.5 μm
Temperature: 40° C.
Condition F: Elution A/B=95/5–35/65
Mobile phase: A: Water (0.05% TFA), B: ACN (0.05% TFA)
Mobile phase ratio: 5% B within 0-3 min, linear gradient elution 5-65% B within 20 min
Velocity: 1.2 ml/min
Column: SunFire C18, 4.6*150 mm, 3.5 μm
Condition G: Elution A/B=80/20–20/80
Mobile phase: A: Water (0.01% TFA), B: ACN(0.01% TFA)
Mobile phase ratio: 20% B within 0-3 min, linear gradient elution 20-80% B within 20 min
Velocity: 1.0 ml/min
Column: SunFire C18, 4.6*150 mm, 3.5 μm
Temperature: 40° C.
Condition H: Elution A/B=50/50–0/100
Mobile phase: A: Water (0.05% TFA), B: ACN (0.05% TFA)
Mobile phase ratio: 50% B within 0-3 min, linear gradient elution 50-100% B within 20 min
Velocity: 1.0 mL/min
Column: XBridge Peptide BEH C18, 4.6*150 mm, 3.5 μm
Column temperature: 40° C.
Condition I: Elution A/B=80/20–5/95
Mobile phase: A: Water (0.01% TFA), B: ACN (0.01% TFA)
Mobile phase ratio: 20% B within 0-2 min, linear gradient elution 20-95% B within 25 min
Velocity: 1.0 mL/min
Column: SunFire C18, 4.6*150 mm, 3.5 μm
Column temperature: 40° C.
Condition J: Elution A/B=95/5–35/65
Mobile phase: Water (0.05% TFA), B: ACN (0.05% TFA)
Mobile phase ratio: 5% B within 0-3 min, linear gradient elution 5-65% B within 20 min
Velocity: 1.0 mL/min
Column: XBridge Peptide BEH C18, 4.6*150 mm, 3.5 μm
Column temperature: 40° C.
Condition K: Elution A/B=50/50–0/100
Mobile phase: A: A: Water (0.01% TFA), B: ACN (0.01% TFA)
Mobile phase ratio: 50% B within 0-3 min, linear gradient elution 50-100% B within 20 min
Velocity: 1.0 ml/min
Column: SunFire C18, 4.6*150 mm, 3.5 μm
Column temperature: 40° C.
Condition L: Elution A/B=80/20–5/95
Mobile phase: A: Water (0.05% TFA), B: ACN (0.05% TFA)
Mobile phase ratio: 20% B within 0-2 min, linear gradient elution 20-95% B within 25 min
Velocity: 1.0 ml/min
Column: XBridge Peptide BEH, 4.6*150 mm, 3.5 μm
Column temperature: 40° C.
Condition M: Elution A/B=80/20–20/80
Mobile phase: A: Water (0.05% TFA), B: ACN (0.05% TFA)
Mobile phase ratio: 20% B within 0-1 min, linear gradient elution 20-80% B within 20 min
Velocity: 1.0 mL/min
Column: XBridge Peptide BEH C18, 4.6*150 mm, 3.5 μm
Column temperature: 40° C.
Condition N: Elution A/B=70/30–0/100

Mobile phase: A: Water (0.05% TFA), B: ACN (0.05% TFA)

Mobile phase ratio: 30% B within 0-3 min, linear gradient elution 30-100% B within 20 min Velocity: 1.0 mL/min Column temperature: 40° C.

Column: XBridge Peptide BEH C18, 4.6*150 mm, 3.5 μm

Condition O: Elution A/B=65/35−0/100

Mobile phase: A: Water (0.05% TFA), B: ACN (0.05% TFA)

Mobile phase ratio: 35% B within 0-1 min, linear gradient elution 35-100% B within 20 min Velocity: 1.0 mL/min Column temperature: 40° C.

Column: XBridge Peptide BEH C18, 4.6*150 mm, 3.5 μm

Condition P: Elution AB=65/25−45/55

Mobile phase: A: Water (0.05% TFA), B: ACN (0.05% TFA)

Linear gradient elution 25-45% B within 30 min

Velocity: 1.0 mL/min

Column temperature: 40° C.

Column: XBridge Peptide BEH C18, 4.6*150 mm, 3.5 μm

Condition Q: Elution AB=82/18−52/48

Mobile phase: A: Water (0.05% TFA), B: ACN (0.05% TFA)

Linear gradient elution 25-45% B within 30 min

Velocity: 1.0 mL/min

Column temperature: 40° C.

Column: XBridge Peptide BEH C18, 4.6*150 mm, 3.5 μm

Effect Embodiment 1 Determination of kiss1 Receptor (GPR54) Binding Activity of kiss1 Receptor (GPR54) Agonist The binding activity test of each compound from the above the embodiments with kiss1 receptor (GPR54) was performed by fluorescence energy resonance transfer (FRET) detection technology to detect $EC_{50}$ values of polypeptides and peptide analogs. The cells used in this experiment were NFAT-bla CHO-K1 cells (k1720, invitrogen, thermosher) that express human kiss1 receptor (GPR54). The specific operations were as follows:

Day 1: Seeding Cells in Plate

1. Microscope (CKX41, OLYMPUS), object lens×4 times, ocular lens×10 times. The cells were ensured in a good condition.

2. Digesting the cells, adding 3 ml of 0.05% pancreatin into a culture dish; cells were placed in a 37° C., 5% $CO_2$ incubator for 2 minutes (Thermo Fisher). After the cells became round under the microscope, 7 ml of culture medium was added. The formula of culture medium was as follows: DMEM 90%, dialzedfbS 10, NEAA 0.1 mM, HEPES 25 mM, Penicillin 100 U/ml, Streptomycin 100 μg/ml, pH 7.3. After blowing and stiring, it was transferred to 15 mL centrifuge tube (430790, Corning). Centrifuge at 1000 rpm for 5 min (5810R, Eppendorf) and the supernatant was discard.

3. Adding 7 mL of culture medium (DMEM+0.1% BSA), it was pipetting into single cell suspension, after counting with Bio-RAD counter, the cell density was adjusted to 312,500 cells/ml.

4. Cells were inoculated into 384 well plates at 32 μL per well, and the cell number was controlled at 10000 cells/well. 32 μl of culture medium was added into the blank control.

Day 2: Dosing and Data Analysis 1. 1000× Compound Plate Configuration

1) The compound to be tested was prepared into 50 mM working solution with DMSO.

2) 40 μl of the working solution of the compound to be tested was added into column 2 of row A-H of U-shaped 96-well plate (3797, comings), and 60 μl of DMSO was added into column 3-11. 20 μl of compound solution was sucked from the second column to the third column with a multichannel pipette blowing and stiring evenly; 20 μl of compound solution was absorbed from the third column with a multichannel pipette, then added into the fourth column, blowed and stirred to mix well; the compound was serially diluted 4-fold to a total of 10 concentrations. Column 1 and column 12 of 96-well plates were supplemented with 40 μl DMSO.

2. Intermediate Plate Configuration

1) AU-shaped 96-well plate was used, 199 μL of culture medium (DMEM+0.1% BSA) was added to each well, 1 μL of diluted compound (or DMSO) was sucked from 1000× compound plate and added into the 96-well plate at the corresponding position, blowed and stirred to mix well.

2) Homemade positive compounds and compounds to be tested were added. The cell culture plate was took out from the incubator and cells state was observed under microscope. Diluted compound in the intermediate plate or DMSO was added into the cell, 8 μl per well.

3) Cells were cultured in 37° C. and 5% $CO_2$ for 4 hours.

3. The Substrate was Added to Detect the Binding of the Drug to the Receptor 1) 1 μmol/L CCF-4 AM solution and buffer solution B, C, D were equilibrated to room temperature. LiveBLAZER™-FRET B/G Loading Kit (K1095, thermo Fisher) containing CCF-4 AM and solution B, solution C, solution D were also available from Invitrogen (K1157, thermo Fisher).

2) 6× loading solution was prepared: 6 μl of CCF-4 AM dissolved solution A, 60 μl of solutionb, 904 μl of solutionc, and 30 μl of solution D were pipetted into EP tube, blowed and stirred to mix well.

3) 8 μl of the above-mentioned liquid was sucked with a multichannel pipette, added into a 96-well plate, and incubated for 2 hours at room temperature.

4) The PerkinElmer detector was used to detect the luminous signals of each hole. FI mode, λex=409 nm, λem1=460 nm, λem2=530 nm.

4. Data Processing Using Graphpad Prism 5 (GraphPad Software. Inc)

Effective rate %=(Signal−Min)/(Max−Min)×100%. Max: the maximum binding value of high concentration positive compound to kiss1 receptor. Min: Minimum value of no binding of 0.1% DMSO to receptor. Signal: the signal value at the corresponding concentration of the compound. The $EC_{50}$ of the corresponding compound was obtained by fitting the parameter curve with the concentration of the compound and the corresponding effective rate, as shown in Table 3.

TABLE 3

| $EC_{50}$ of each polypeptide | |
| --- | --- |
| Polypeptide number | GPR54 $EC_{50}$/nM |
| YA-156 | 0.045 |

The EC$_{50}$ of parts of the compounds listed in Table 3 was superior to TAK448, showing strong activity, indicating that the compounds of the present disclosure can effectively bind kiss1 receptor (GPR54) at the level of in vitro biochemical experiments, so the compounds of the present disclosure has the potential to become effective therapeutic drugs for tumors.

Effect Embodiment 2 Experimental Data on Plasma Stability of Some Compounds

1. Preparation of 50 mM phosphate buffer:

The 5.750 g Na$_2$HPO$_4$, 1.141 g NaH$_2$PO$_4$. and 4.095 g NaCl (Shanghai Titan) weighed was dissolved in 1000 mL ultrapure water and the pH was adjusted to 7.4 to give 50 mM phosphate buffer containing 70 mM NaCl. The prepared phosphoric acid buffer solution was stored in the refrigerator at 4° C. and was valid for one week.

2. Preparation of compound stock solution:

1). 5 mg/mL of test compound: 5 mg of compound was weighted and dissolved in 1 mL of DMSO.

2). 20 mM control: 2.728 mg of Fuka was dissolved in 0.5 mL of DMSO. 3.878 mg of benzalkonium bromide was dissolved in 0.5 mL of DMSO (Amresco).

3. Preparation of experimental plasma:

The frozen plasma (human: Shanghai wise chemistry; Rats and mice: Shanghai Sciple-Bikai; Dogs and monkeys: Suzhou Xishan Zhongke) were taken out of the −80° C. refrigerator, immediately placed in a 37° C. water bath, slightly shaken to melt it, then the thawed plasma was poured into a centrifuge tube, centrifuged at 3000 rpm for 8 min, and the supernatant was taken for experiments. The pH value of plasma was detected by a pH Meter & Sensor (METTLER TOLEDO). Only plasma with a pH value between 7.4 and 8 was used in the experiment. The plasma was placed on an ice bath for later use.

4. Preparation of administration solution:

1). 125 g/ml test compound solution: 5 μL of 5 mg/mL test compound (see step 2) was added into 195 μL DMSO; 500 μM control solution: 20 mM control stock solution (see step 2) was added to 195 μL DMSO.

2). 0.5% BSA phosphate buffer solution: 0.05 g BSA was added to 10 mL phosphate buffer solution (see step 1);

3). 5 g/ml of test compound administration solution: 40 μL of 125 μg/mL of test compound solution was added into 960 μL 0.5% BSA phosphate buffer solution, stirred and mixed evenly, and the administration solution was preheated in a 37° C. water bath for 5 minutes.

20 μM reference substance administration solution: 40 μL of 500 μM reference substance administration solution was added into 960 μL 0.5% BSA phosphate buffer solution, stirred and mixed evenly, and the administration solution was preheated in a 37° C. water bath for 5 minutes.

5. 10 μL of 5 μg/mL of the test compound and 20 μM of the control substance administration solution were respectively added to the wells set at different time points (0 minutes, 1 hour, 2 hours and 4 hours) on the 96-well plate, and the number of duplicate samples was 3.

6. 500 μL of ACN (IS) containing 5% FA was added to the well set at 0 minute hour, then 90 μL of plasma was added, after mixing, sealing film was pasted and placed at 4° C. (number of duplicate samples was 3).

7. 90 μL of plasma was added to the wells with set time points of 1 hour, 2 hours and 4 hours respectively, the number of duplicate samples was 3, and timing was started (the final concentration of the test compound was 500 ng/ml; The control was 2 μM).

8. Then, when the timer shows 1 hour, 2 hours and 4 hours, 500 μL of ACN (IS) solution containing 5% FA were added to the holes, respectively, at corresponding time points to terminate the reaction, and after mixing, sealing films were pasted and placed at 4° C.

9. All samples (0 minutes, 1 hour, 2 hours and 4 hours) at different time points on a 96-well plate were shaken for 10 minutes at 600 rpm/min on an oscillator (MTS 2/4, IKA), and then the samples were centrifuged for 15 minutes at 5594× g in a centrifuge (Multifuge×3R, thermo Fisher).

10. 150 μL of supernatant was taken from the centrifuged sample and sent to LC-MS/MS for analysis (conventional polypeptide LC-MS/MS analysis method). The calculated half-life of the corresponding compounds were shown in Table 4.

TABLE 4

Experimental Data on Plasma Stability of Compounds

| Polypeptide number | Rat plasma (T½ (h)) |
|---|---|
| YA-156 | 44.38 |

Although specific embodiments of the present disclosure have been described above, those skilled in the art should understand that these were merely embodiments and various changes or modifications can be made to these embodiments without departing from the principles and essence of the present disclosure. Therefore, the scope of protection of the present disclosure was defined by the appended claims.

What is claimed is:

1. A method for treating diseases related to kisspeptin receptors in a subject in need thereof, comprising administering an effective amount of the compound YA-156, a pharmaceutically acceptable salt thereof, a tautomer thereof, or a solvate thereof, wherein the compound YA-156 is shown below:

Palm-PEG8-Gly-Gly-(D-Tyr)-Hyp-Asn-Thr-Phe-azaGly-Leu-Arg(Me)-Trp-NH$_2$, wherein Palm is palmitoyl, wherein said disease related to kisspeptin receptors is one or more of hormone-related diseases, wherein hormone-related disease is endometriosis.

* * * * *